(12) United States Patent
Merli et al.

(10) Patent No.: US 7,462,743 B2
(45) Date of Patent: Dec. 9, 2008

(54) POLYMORPHS OF MEMANTINE HYDROCHLORIDE

(75) Inventors: Valeriano Merli, Cremella Lecco (IT); Paola Daverio, Milan (IT); Adrienne Kovacsne-Mezei, Debrecen (HU); Judith Aronhime, Rehovot (IL)

(73) Assignee: Teva Pharmaceutical Fine Chemicals S.r.l., Bulciago (LC) (IT)

( * ) Notice: Subject to any disclaimer, the term of this patent is extended or adjusted under 35 U.S.C. 154(b) by 185 days.

(21) Appl. No.: 11/331,263

(22) Filed: Jan. 11, 2006

(65) Prior Publication Data

US 2006/0217573 A1 Sep. 28, 2006

Related U.S. Application Data

(60) Provisional application No. 60/642,957, filed on Jan. 11, 2005, provisional application No. 60/677,599, filed on May 3, 2005.

(51) Int. Cl.
*C07C 211/35* (2006.01)
(52) U.S. Cl. .................................... 564/459
(58) Field of Classification Search ............ None
See application file for complete search history.

(56) References Cited

U.S. PATENT DOCUMENTS 3,391,142 A   7/1968  Mills et al.
4,122,193 A  10/1978  Scherm et al.
5,061,703 A  10/1991  Bormann et al.
5,599,998 A   2/1997  Kraus
5,614,560 A   3/1997  Lipton

FOREIGN PATENT DOCUMENTS

| CN | 1335299 | | 2/2002 |
|---|---|---|---|
| CN | 1400205 | | 3/2003 |
| CZ | 282 398 | | 5/1997 |
| JP | 2002 275142 | | 9/2002 |
| WO | WO 2005/069742 | * | 4/2005 |
| WO | WO 2005/062724 | | 7/2005 |
| WO | WO-2007/132476 A2 | | 11/2007 |

OTHER PUBLICATIONS

Gerzon, et al. "The Adamantyl Group in Medicinal Agents. I. Hypoglycemic N-Arylsulfonyl-N'-Adamantylureas" *J. Medicinal Chemistry*, vol. 6, p. 760-763 (1963).
Henkel, et al. "Structure-Anti-Parkinson Activity Relationships in the Aminoadamantanes. Influence of Bridgehead Substitution" *J. Medicinal Chemistry*, vol. 25, p. 51-56, (1982).

* cited by examiner

*Primary Examiner*—Samuel A Barts
(74) *Attorney, Agent, or Firm*—Kenyon & Kenyon LLP (57) ABSTRACT

A crystalline Form II of memantine hydrochloride, pharmaceutical compositions containing crystalline Form II, and methods of preparing crystalline Forms I and II of memantine hydrochloride are provided.

27 Claims, 5 Drawing Sheets

POLYMORPHS OF MEMANTINE HYDROCHLORIDE

RELATED APPLICATIONS

This application claims benefit of U.S. Provisional Patent Application No. 60/642,957, filed Jan. 11, 2005, and U.S. Provisional Patent Application No. 60/677,599, filed May 3, 2005, the contents of which are incorporated herein by reference.

FIELD OF THE INVENTION

The present invention is directed to a crystalline Form II of 1-amino-3,5-dimethyladamantane hydrochloride ("memantine hydrochloride"), to methods of making the crystalline form, and to pharmaceutical compositions comprising the crystalline Form II of memantine hydrochloride, as well as methods for the preparation of memantine HCl crystal Form I.

BACKGROUND

Memantine hydrochloride, 1-amino-3,5-dimethyladamantane hydrochloride, is one of a small group of tricyclic antiviral drugs (TAV). Memantine also provides good and persistent activation of central nervous N-methyl-D-aspartate (NMDA) receptors, and, thus, can be used in the treatment of Parkinson's disease and Alzheimer's disease. There is increasing evidence that memory loss and dementia in Alzheimer's disease are related to malfunctioning of the signals that pass messages between the nerve cells in the brain. In particular, the excessive activity of a chemical called glutamate contributes to the symptoms of Alzheimer's, as well as the progression of this disease. Glutamate acts on the NMDA receptors that are found on nerve cells in the brain. These receptors and nerve cells are involved in transmitting nerve messages in the brain that are important in learning and memory. Reportedly, Glutamate damages the nerve cells by excessively stimulating the NMDA receptors. Memantine works by blocking the NMDA receptors in the brain, blocking the excessive activity of glutamate, but allowing the normal activation of the NMDA receptors that occurs when the brain forms a memory. Memantine may therefore improve brain functioning in Alzheimer's disease, and may also block the glutamate activity that could cause further damage to the brain cells. Memantine is licensed to treat moderately severe to severe Alzheimer's disease. Studies have demonstrated that memantine causes a small improvement or stabilization in the cognitive functioning, i.e., thinking, learning, and memory, and the daily functioning of Alzheimer's patients.

The chemical structure of memantine hydrochloride may be represented by:

There is no known prior art disclosure of polymorphism in memantine hydrochloride. Examples of the crystallization of memantine hydrochloride are reported in a few patents, but none of the patents disclose any polymorphic forms. For example, U.S. Pat. No. 3,391,142 discloses the precipitation of memantine hydrochloride from an anhydrous ether solution and crystallization of the crude product in an alcohol-ether mixture. U.S. Pat. No. 4,122,193 discloses the precipitation of memantine hydrochloride precipitation by bubbling hydrochloric acid in an ether solution of memantine free base, and CZ 282398 discloses adding aqueous hydrochloric acid to toluenic solution of memantine free base to provide the hydrochloride. All prior art methods for the preparation of memantine hydrochloride result in the formation of a single crystalline form, herein Form I, characterized by X-ray diffraction (XRD) having peaks at about: 6.3, 12.5, and 18.8±0.2 degrees 2 theta, and further characterized by peaks at about 11.0, 14.2, 16.6, 21.8, 22.7, 24.4, and 27.4±0.2 degrees 2 theta.

The present invention relates to the solid state physical properties of memantine hydrochloride. These properties can be influenced by controlling the conditions under which memantine hydrochloride is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA), and differential scanning calorimetry (DSC), and can be used to distinguish some polymorphic forms from others. A particular polymorphic form may also give rise to distinct spectroscopic properties that may be detectable by powder X-ray crystallography, solid state $^{13}$C NMR spectrometry, and infrared spectrometry.

Thus, the discovery of new polymorphic forms of a pharmaceutically useful compound provides a new opportunity to improve the performance characteristics of a pharmaceutical product. It enlarges the repertoire of materials that a formulation scientist as available for designing, for example, a pharmaceutical dosage form of a drug with targeted release profile or other desired characteristic. There is a need in the art for additional crystalline forms of memantine hydrochloride.

SUMMARY OF THE INVENTION

The present invention is directed to a crystalline of memantine hydrochloride, designated herein as Form II, characterized by at least one of an X-ray powder diffraction pattern, having peaks at about 6.7, 13.3, and 20.2±0.2 degrees 2θ, and a DSC thermogram, having three endothermic peaks at about 50° C., 90° C., and 341° C.

Form II of memantine hydrochloride can be further characterized by a TGA thermogram showing a weight loss of about 7.5 to about 8.5 percent by weight up to about 117° C. that corresponds to the Karl Fischer titration.

The present invention is also directed to a method for producing memantine hydrochloride Form II, comprising: admixing acetone with a solution of memantine hydrochloride and water; removing the water and acetone to obtain memantine hydrochloride Form II; and recovering memantine hydrochloride Form II.

The present invention is further directed to a pharmaceutical formulation comprising memantine hydrochloride Form II and a pharmaceutically acceptable excipient.

The present invention is also directed to a method of treating a patient suffering from Parkinson's disease or Alzheimer's disease, by administering a therapeutically effective amount of the pharmaceutical formulation described above.

The present invention provides a method for producing memantine hydrochloride Form I comprising providing a solution of memantine hydrochloride in $C_{1-4}$ alcohols; exposing the solution to an anti-solvent selected from the group consisting of $C_{1-5}$ ketones or $C_{1-5}$ alkyl esters to obtain a precipitate; and recovering memantine hydrochloride Form I.

The present invention provides another method for producing memantine hydrochloride Form I, comprising providing a solution of memantine hydrochloride in a solvent selected from the group consisting of water, $C_{1-5}$ alcohols, DMF, and DMSO, and admixing an anti-solvent selected from the group consisting of $C_{6-10}$ aromatic hydrocarbons, open or closed-chained $C_{1-5}$ alkyl ethers, $C_{1-5}$ ketones, $C_{1-5}$ amides, carbonate, esters, and amides to cause formation of precipitation; and recovering memantine hydrochloride Form I.

The present invention provides yet another method for producing memantine hydrochloride Form I, comprising: providing a solution of memantine HCl in a solvent selected from the group consisting of water, $C_{1-4}$ alcohols, $C_{6-10}$ aromatic hydrocarbons, $C_{1-4}$ halo-substituted hydrocarbons, esters, and $C_{1-5}$ alkyl ethers; cooling the solution to initiate precipitation; and recovering memantine hydrochloride Form I.

The present invention provides yet another method for producing memantine hydrochloride Form I by concentrating a solution of memantine hydrochloride and a solvent selected from the group consisting of $C_{1-4}$ alcohols and halo-substitution thereof; and recovering memantine hydrochloride Form I.

DETAILED DESCRIPTION OF THE INVENTION

As used herein, the terms "memantine hydrochloride Form I" and "memantine HCl Form I" refer to the crystalline form obtained by performing the crystallization processes described in the prior art, which is also the commercially available anhydrous form of memantine hydrochloride.

The present invention is directed to a crystalline form of memantine hydrochloride, designated herein as Form II, to methods of making memantine hydrochloride Forms I and II, to pharmaceutical compositions of memantine hydrochloride Form II, and to methods of treatment using memantine hydrochloride Form II.

The present invention provides memantine hydrochloride crystalline form, denominated Form II, characterized by at least one of an X-ray powder diffraction pattern having peaks at about 6.7, 13.3, and 20.2±0.2 degrees 2θ; an infrared spectrum having peaks at about 3446, 3396, 1621, and 1532 cm$^{-1}$, and a DSC thermogram having three endothermic peaks at about 50° C., 90° C., and 341° C.

Figure 1:
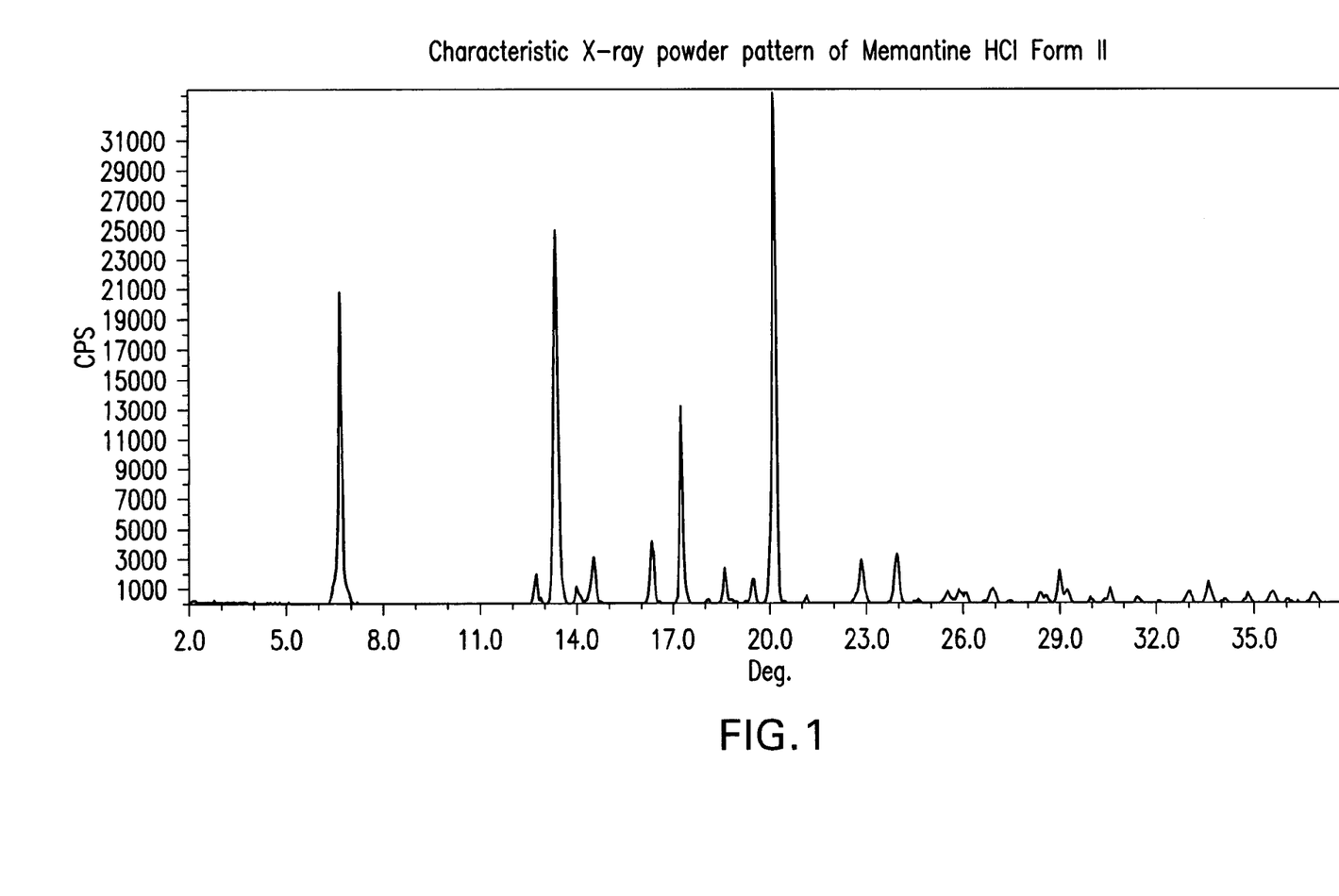
FIG. 1 illustrates a characteristic X-ray powder diffraction pattern of Memantine HCl crystal Form II.

Memantine hydrochloride Form II may be further characterized by an X-ray powder diffraction pattern having peaks at about 14.5, 17.2, 18.6, 22.9, 23.9, and 29.0±0.2 degrees 2θ, substantially as illustrated in FIG. 1.

Figure 2:
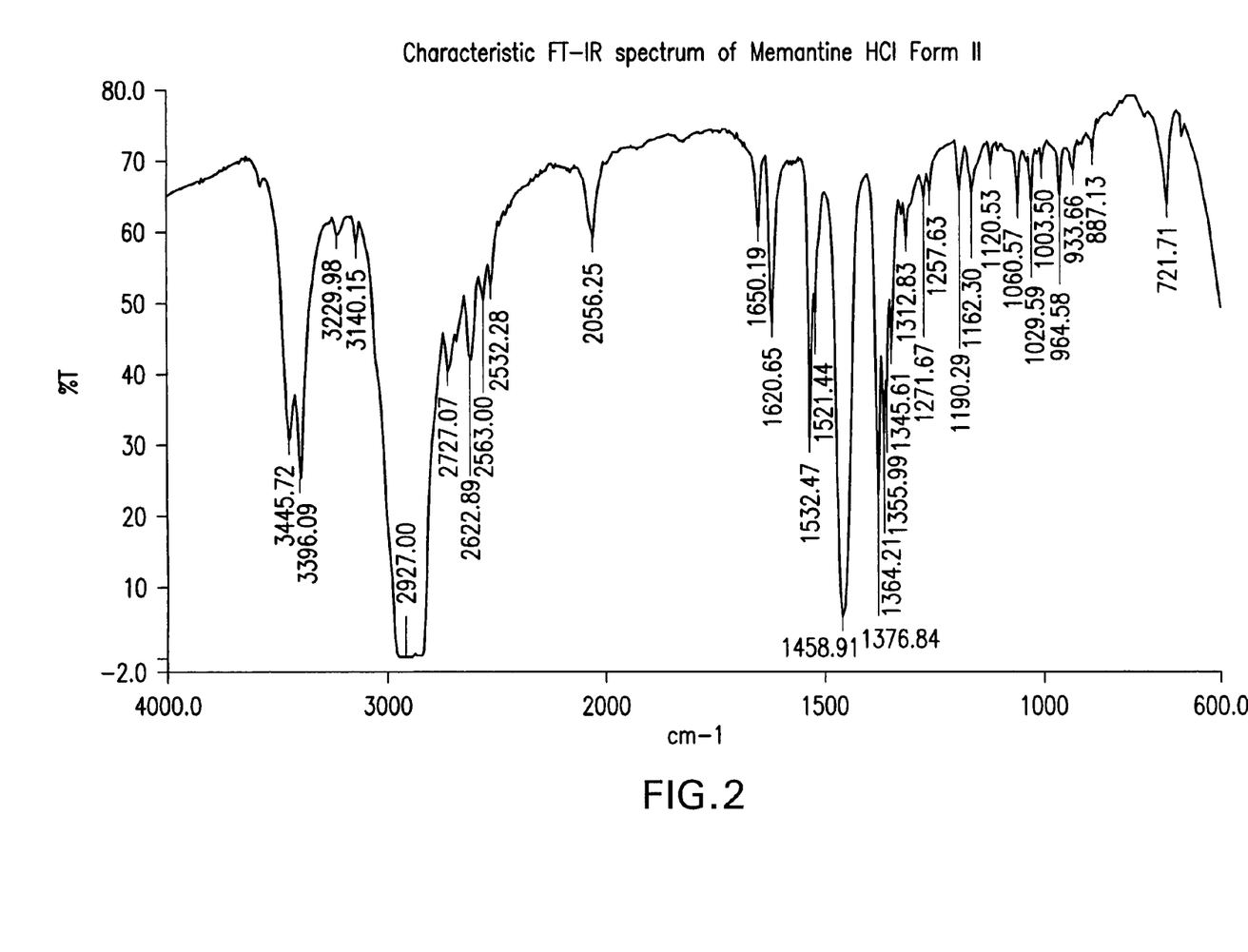
FIG. 2 illustrates a characteristic FT-IR spectrum of memantine HCl crystal Form II.

Form II of memantine hydrochloride can also be further characterized by an infrared spectrum having peaks at about 2056, 1650, 1521, 1384, 1190, 1162, 1061, 1030, 965, 934, and 721 cm$^{-1}$, substantially as illustrated in FIG. 2.

Figure 3:
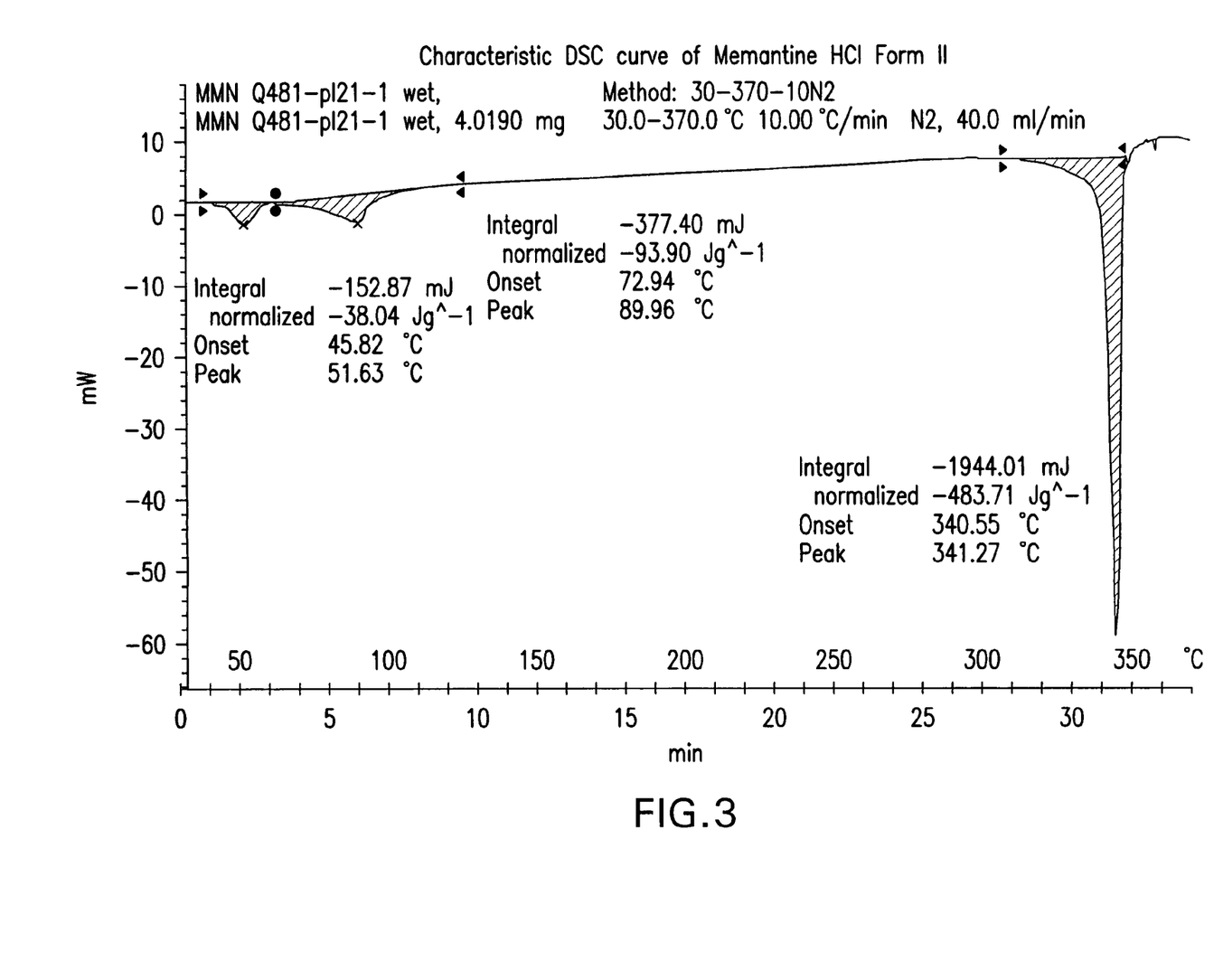
FIG. 3 illustrates a characteristic DSC curve of memantine HCl crystal Form II.

The three endothermic peaks at 50° C., 90° C., and 341° C. in the DSC thermogram of Form II indicate solvent removal, water removal, and the melting of the sample, respectively. As the material decomposes during melting, such that it becomes charred, no exact melting point can be given. A characteristic DSC thermogram of memantine hydrochloride Form II is illustrated in FIG. 3.

Figure 4:
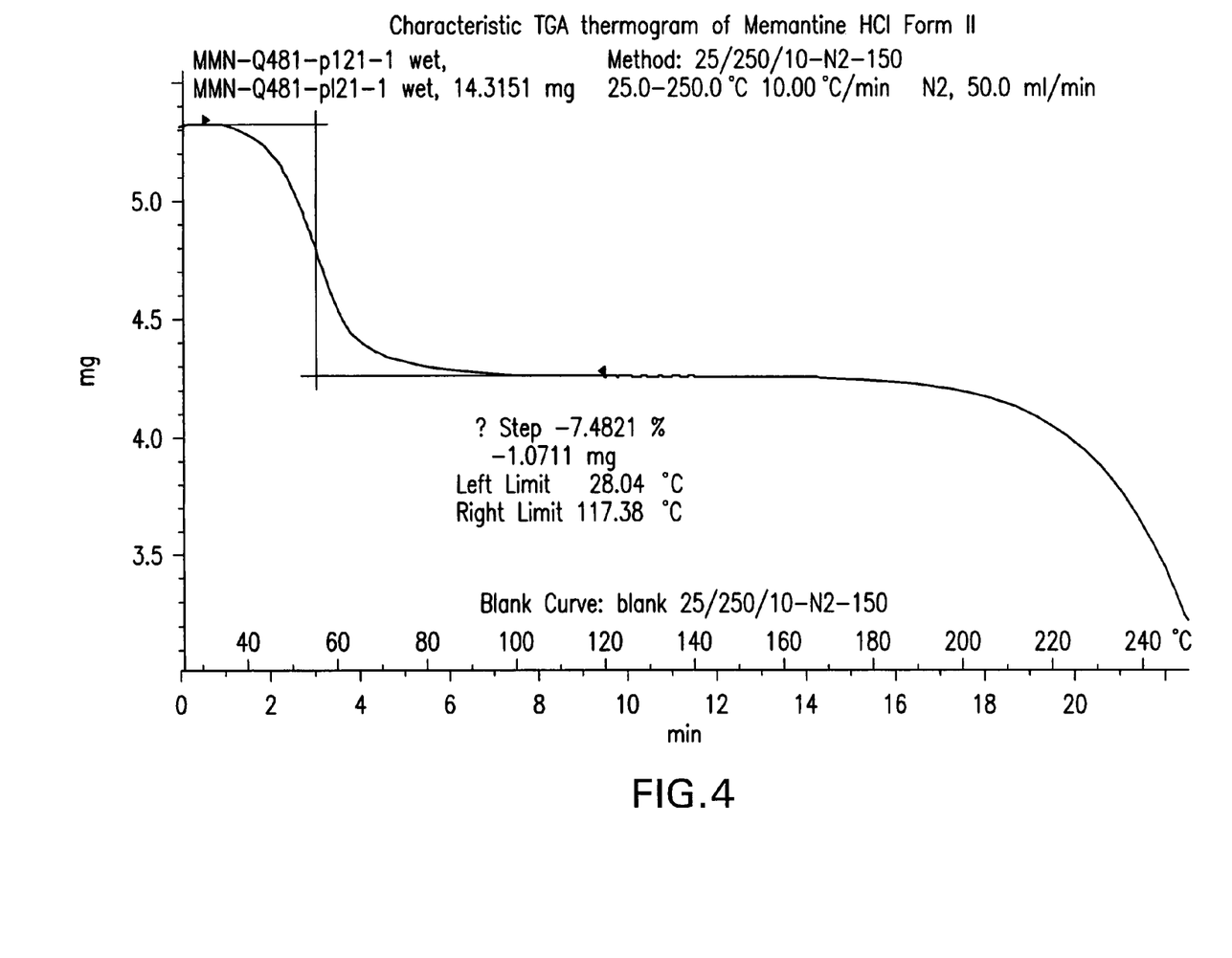
FIG. 4 illustrates a characteristic TGA curve of memantine HCl crystal Form II.
Figure 5:
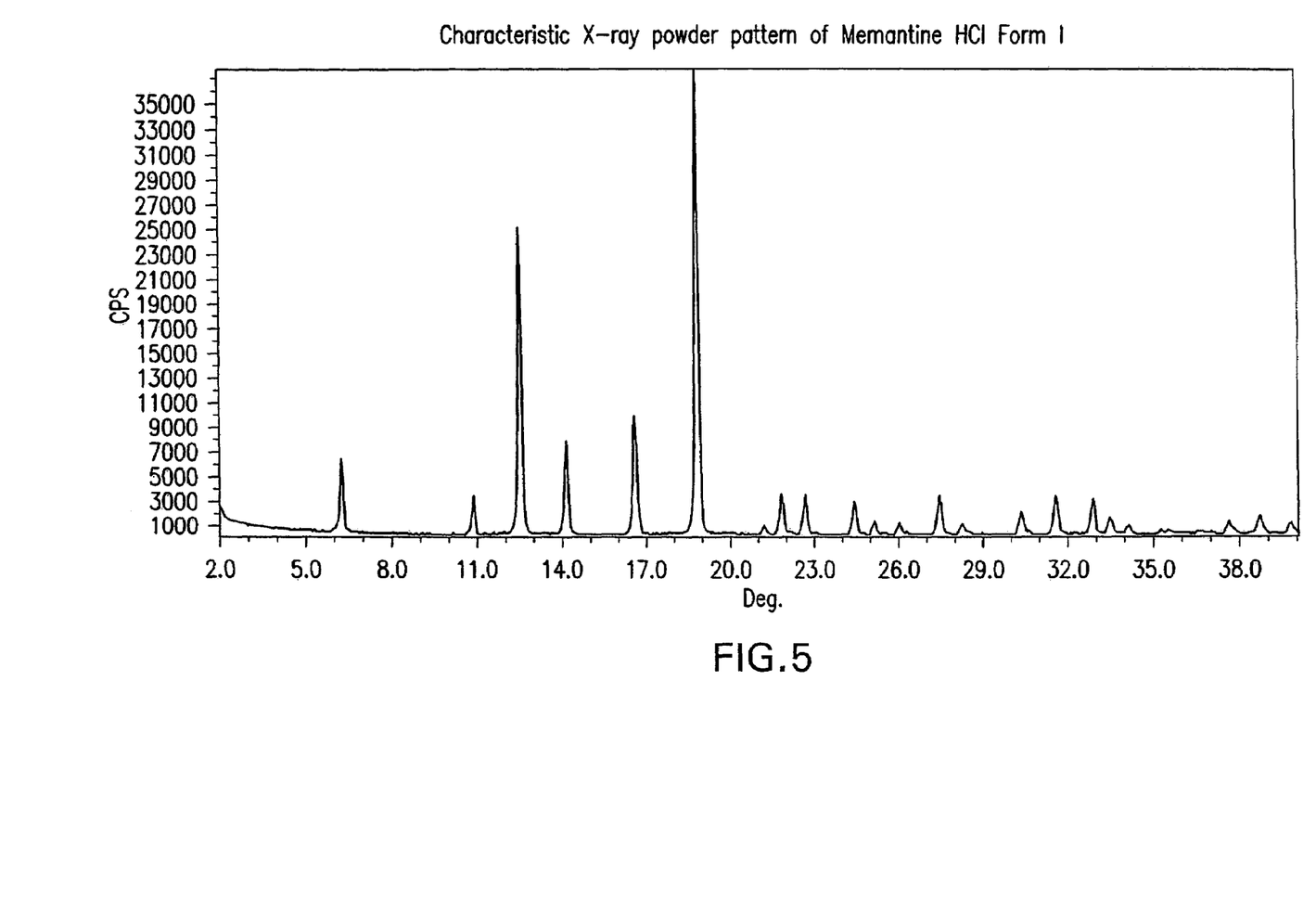
FIG. 5 illustrates a characteristic X-ray powder diffraction pattern of Memantine HCl crystal Form I.

A TGA thermogram of Form II of memantine hydrochloride shows a weight loss of about 7.5 to about 8.5 percent by weight up to about 117° C. that corresponds to the Karl Fischer titration. This weight loss corresponds to the theoretical value of the water content of memantine hydrochloride monohydrate, as Form II is the monohydrate of memantine hydrochloride. The Form II TGA curve also shows a weight loss at about 200° C., indicating the slow decomposition of the material. A characteristic TGA thermogram for memantine hydrochloride Form II is illustrated in FIG. 4.

Crystals of memantine hydrochloride have an irregular shape, and a size of up to about to 200 μm, preferably, up to about 150 μm, more preferably, up to about 100 μm, and, most preferably, up to about 75 μm.

The present invention also provides a method for producing memantine hydrochloride Form II, comprising: admixing acetone with a solution of memantine hydrochloride and water; removing the water and acetone to obtain memantine hydrochloride Form II; and recovering memantine hydrochloride Form II.

The solution of memantine HCl may be prepared by suspending memantine HCl in water, preferably in the amount of about 0.4 to about 0.6 mol memantine hydrochloride/liter water. Depending on the amount of water used, heating to a temperature of about 50° C. to about 100° C. can aid in dissolution. Preferably, heating is to a temperature of about 80° C. to about 90° C., and, more preferably, to about 85° C. to about 90° C.

Preferably, before acetone is admixed, the solution is cooled, most preferably to a temperature of about 50° C. to about 55° C. Preferably, the acetone is in the general range of concentration of about 0.05 to about 2 mole memantine hydrochloride/liter acetone, most preferably about 0.6 mol/liter. The solution is then cooled, preferably, to about room temperature, and maintained to allow precipitation of memantine HCl and evaporation of the solvent for about three days to about three months, most preferably about one month.

Removing the acetone and water may be performed by any means known in the art however, preferably by spontaneous evaporation.

Recovering memantine hydrochloride Form II can be performed by any method known in the art. Preferably by filtering and washing the residue.

The memantine hydrochloride used as starting material may be obtained commercially, or by any method known in the art, such as the one described in co-pending U.S. application Ser. No. 11/330681, filed Jan. 11, 2006, which claims benefit of U.S. Provisional Patent Application No. 60/642,957, filed Jan. 11, 2005.

The present invention further provides a pharmaceutical formulation comprising memantine hydrochloride Form II and a pharmaceutically acceptable excipient.

The present invention also provides a method of treating a patient suffering from Parkinson's disease or Alzheimer's disease, by administering a therapeutically effective amount of the pharmaceutical formulation described above.

The present invention provides a method for producing memantine hydrochloride Form I comprising providing a solution of memantine hydrochloride in $C_{1-4}$ alcohols; exposing the solution to an anti-solvent selected from the group consisting of $C_{1-5}$ ketones or $C_{1-5}$ alkyl esters to obtain a precipitate; and recovering memantine hydrochloride Form I.

Preferably, the $C_{1-4}$ alcohol in the memantine hydrochloride solution is methanol. Preferably, the $C_{1-5}$ ketone is acetone. Preferably, the $C_{1-5}$ alkyl ester is methyl acetate. Preferably, exposing the solution is by providing a saturated atmosphere of the anti-solvent. Memantine hydrochloride Form I may be recovered by any method known in the art, such as filtering and drying the obtained product.

The present invention provides another method for producing memantine hydrochloride Form I, comprising: providing a solution of memantine hydrochloride in a solvent selected from the group consisting of water, $C_{1-5}$ alcohols, DMF, and DMSO; and admixing an anti-solvent selected from the group consisting of $C_{6-10}$ aromatic hydrocarbons, open or closed-chained $C_{1-5}$ alkyl ethers, $C_{1-5}$ ketones, $C_{1-5}$ amides, carbonate, esters, and amides to cause formation of precipitation; and recovering memantine hydrochloride Form I.

Preferably, the solvent is selected from the group consisting of MeOH, IPA, n-butanol, water, ethanol, DMSO, and DMF. Preferably the anti-solvent is selected from the group consisting of Toluene, isopropylether, n-BuOAc, AcOEt, acetone, acetonitrile, DMC, THF, MTBE, and MEK. At times, precipitation may be by slow precipitation or evaporation.

Recovery may be performed by any means known in the art. In addition, memantine hydrochloride Form I recovered may be either wet or dry. When water is used as a solvent, and toluene or MEK is used as an anti-solvent, wet memantine HCl comprises a mixture of Forms I and II. Upon drying, memantine HCl Form I is obtained.

The present invention provides yet another method for producing memantine hydrochloride Form I, comprising: providing a solution of memantine HCl in a solvent selected from the group consisting of water, $C_{1-4}$ alcohols, $C_{6-10}$ aromatic hydrocarbons, $C_{1-4}$ halo-substituted hydrocarbons, esters, and $C_{1-5}$ alkyl ethers; cooling the solution to initiate precipitation; and recovering memantine hydrochloride Form I.

Preferably, the solvent is selected from the group consisting of water, DMF, n-butanol, 2-butanol, n-pentanol, chloroform, Ethyl acetate, acetone, esters, water, MTBE, DMC, and IPA. Optionally, solution may be obtained by heating. When ethyl acetate is used, a saturated atmosphere of hydrochloride gas can be used to initiate precipitation.

Recovery may be performed by any means known in the art. In addition, memantine hydrochloride Form I recovered may be either wet or dry.

The present invention provides yet another method for producing memantine hydrochloride Form I by concentrating a solution of memantine hydrochloride and a solvent selected from the group consisting of $C_{1-4}$ alcohols and halo-substitution thereof, and recovering memantine hydrochloride Form I.

Concentration of the solution may be performed by any method known in the art, such as concentration or evaporation. The evaporation process may be a slow evaporation process. Memantine hydrochloride Form I may be recovered by any methods known in the art. When wet memantine HCl is recovered, in the cases where ethanol or ethanol-dichloromethane are used as solvents, wet memantine HCl comprises a mixture of Form I and Form II.

Examples of the various solvents and conditions that may be used in the formation of memantine hydrochloride Form I are set forth in Tables 1 to 4.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups, and suspensions. Suitable forms of parenteral administration include an aqueous or non-aqueous solution or emulsion, while, for rectal administration, suitable forms for administration include suppositories with a hydrophilic or hydrophobic vehicle. For topical administration the invention provides suitable transdermal delivery systems known in the art, and for nasal delivery there are provided suitable aerosol delivery systems known in the art.

Pharmaceutical formulations of the present invention contain memantine hydrochloride crystal Form II, as disclosed herein. The pharmaceutical composition may contain only a single form of memantine hydrochloride, or a mixture of various forms of memantine hydrochloride, with or without an amorphous form. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition, and to improve the accuracy of dosing. Excipients that may function as glidants include colloidal silicon dixoide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, memantine hydrochloride and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product, and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form, and prepared by any of the methods well-known in the pharmaceutical arts.

Dosage forms include solid dosage forms like tablets, powders, capsules, suppositories, sachets, troches, and losenges, as well as liquid syrups, suspensions, and elixirs.

The dosage form of the present invention may be a capsule containing the composition, preferably a powdered or granulated solid composition of the invention, within either a hard or soft shell. The shell may be made from gelatin, and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended, and then further mixed in the presence of a liquid, typically water that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Physical Experimental Methodology

The XRD analysis was performed using an ARL X-ray powder diffractometer model X'TRA-030, with a Peltier detector, and a round standard aluminum sample holder with a round zero background quartz plate was used. The scanning parameters were as follows: the range was 2° to 40°2θ with a continuous scan at a rate of 3° per minute. The accuracy of peak positions is defined as ±0.2° due to experimental differences, such as instrumentations, sample preparations, and the like.

Fourier transform (FT-IR) spectroscopy measurements were made on samples in a in Nujol mull on a Perkin-Elmer Spectrum 1000 Spectrometer, at a resolution of 4 $cm^{-1}$ with 16 scans in the range of 4000 to 400 $cm^{-1}$, using an empty cell as a background Differential scanning calorimetry (DSC) measurements were performed on a Mettler Toledo DSC $822^e/700$ with a sample having a weight of about 3 to about 5 mg. The heating rate was 10° C. per minute in a crucible having 1 hole with a nitrogen stream flow rate of about 40 ml per minute over a scan range of from about 30° to about 370° C.

The thermal gravimetric analysis (TGA) was performed on a Mettler Toledo TGA/SDTA $851^e$, with a sample having a weight of about 7 to about 15 mg, at a heating rate of about 10° C. per minute, in a nitrogen gas stream having a flow rate of about 50 ml per minute, over a scan range of about 25° to about 250° C.

The morphology and particle size of single crystals was observed using a Zeiss Axiolab Pol type polarizing light Microscope.

The following non-limiting examples are merely illustrative of the preferred embodiments of the present invention, and are not to be construed as limiting the invention, the scope of which is defined by the appended claims.

EXAMPLES

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Example 1

Preparation of Memantine Hydrochloride Form II

A large number of experiments have been performed to determine the existence of different polymorphs of memantine and its precursor. Only a single different polymorph has been found. The experimental procedure that provides the polymorph is described below A 31 g sample of memantine hydrochloride is loaded into a four necked round bottomed flask with 250 ml of water, forming a suspension. The suspension is warmed to about 85° to about 90° C. to dissolve completely the memantine hydrochloride. The solution is cooled to about 50° to about 55° C., and 1400 ml of acetone, having a temperature of about 40° to about 50° C. is added. No crystallization occurs upon cooling to room temperature. The solution is placed in an opened flask, allowing spontaneous solvent evaporation, and, after a period of about one month, small crystals form at the bottom of the flask. The crystals are filtered and washed, and half are subjected to an XRD analysis wet, and the other half are subjected to an XRD analysis after two days at room temperature and atmospheric pressure. The wet product is memantine hydrochloride Form II, and the dry product is memantine hydrochloride Form I.

A number of crystallization experiments were performed using different solvents and/or solvent mixtures. Both dry and wet products were subjected to XRD analysis. Although most products were dried at room temperature at atmospheric pressure, some were dried under vacuum. The experiments and the results of the experiments are summarized in Tables 1 to 4. All of the samples listed in Table 1 were subjected to XRD analysis as dry products.

Example 2

Preparation of Memantine Hydrochloride Form I Using Solvents and Anti-solvents in Saturated Atmosphere

TABLE 1*

| EXPERIMENT | CONDITIONS | RESIDUE | Crystal form by XRD |
|---|---|---|---|
| Q489-p28-1 | Solvent: Methanol Anti-solvent: Acetone by saturated atmosphere liquid—liquid | Wet | I |
| Q489-p28-2 | Solvent: Methanol Anti-solvent: Acetone by Saturated atmosphere liquid—liquid | Dry | I |
| Q489-p38-1 | Solvent Methanol Anti-solvent AcOMe by Saturated atmosphere liquid—liquid | Wet | I |
| Q489-p38-2 | Solvent Methanol Anti-solvent AcOMe by saturated atmosphere liquid—liquid | Dry | I |

*Samples in Table 1 that were dried, were dried at room temperature and atmospheric pressure.

Example 2

Preparation of Memantine Hydrochloride Form I Using Solvents and Anti-solvents

TABLE 2*

| EXPERIMENT | CONDITIONS | RESIDUE | Crystal form by XRD |
|---|---|---|---|
| Q481-p23 | Crystallization from Solvent: MeOH Anti-solvent: Toluene MeOH: Toluene Toluene:MeOH = 5:1 | Dry Dried at 50° C. u.v. | I |
| Q481-p26 | Crystallization from Solvent: IPA Anti-solvent: isopropylether IPA:isopropylether = 12:5 | Dry | I |

TABLE 2*-continued

| EXPERIMENT | CONDITIONS | RESIDUE | Crystal form by XRD |
|---|---|---|---|
| Q481-p112 | Crystallization from Solvent: n-BuOH Anti-solvent: n-BuOAc | Dry | I |
| Q481-p118 | Crystallization from Solvent: n-BuOH Anti-solvent AcOEt | Dry | I |
| Q481-p121-2 | Crystallization from Solvent: water Anti-solvent acetone | Dry | I |
| Q481-p122-1 | Slow crystallization from Solvent: water Anti-solvent: CH$_3$CN | Wet | I + II |
| Q481-p122-2 | Slow crystallization from Solvent: water Anti-solvent: CH$_3$CN | Dry | I |
| Q481-p124-1 | Solvent evaporation from Solvent: EtOH Anti-solvent: Toluene | Wet | II > I |
| Q481-p124-2 | Solvent evaporation Solvent: EtOH Anti-solvent: Toluene | Dry | I |
| Q481-p125-1 | Crystallization from Solvent: EtOH Anti-solvent: Acetone | Wet | I |
| Q481-p125-2 | Crystallization Solvent: EtOH Anti-solvent: Acetone | Dry | I |
| Q481-p126-1 | Crystallization from Solvent: EtOH Anti-solvent: DMC | Wet | I |
| Q481-p126-2 | Crystallization from Solvent: EtOH Anti-solvent: DMC | Dry | I |
| Q481-p127-1 | Crystallization from Solvent: EtOH Anti-solvent: THF | Wet | I |
| Q481-p127-2 | Crystallization from Solvent: EtOH Anti-solvent: THF | Dry | I |
| Q481-p129-1 | Precipitation from Solvent: EtOH Anti-solvent: MTBE | Wet | I |
| Q481-p129-2 | Precipitation from Solvent: EtOH Anti-solvent: MTBE | Dry | I |
| Q481-p132-1 | Precipitation from Solvent: DMSO Anti-solvent: MTBE | Wet | I |
| Q481-p132-2 | Precipitation from Solvent: DMSO Anti-solvent: MTBE | Dry | I |
| Q481-p133-1 | Crystallization from Solvent: DMF Anti-solvent: MEK | Wet | I |
| Q481-p133-2 | Crystallization from Solvent: DMF Anti-solvent: MEK | Dry | I |
| Q481-p134-3 | Precipitation from- Solvent: 2-BuOH Anti-solvent: MTBE | Wet | I |
| Q481-p134-4 | Precipitation from Solvent: 2-BuOH Anti-solvent: MTBE | Dry | I |
| Q481-p131-1 | Slow crystallization from Solvent: water Anti-solvent: MEK | Wet | II > I |
| Q481-p131-2 | Slow crystallization from Solvent: water Anti-solvent: MEK | Dry | I |

*Samples in Table 2, if not written otherwise, were dried at room temperature and atmospheric pressure.

Example 3

Preparation of Memantine Hydrochloride Form I by Crystallization

TABLE 3*

| EXPERIMENT | CONDITIONS | RESIDUE | Crystal form by XRD |
|---|---|---|---|
| Q481-p9 | Crystallization from water | Dry Dried at 40° C. u.v. | I |
| Q481-p10 | Crystallization from DMF | Dry Dried at 60° C. u.v. | I |
| Q481-p20 | Crystallization from n-BuOH | Dry Dried at 50° C. u.v. | I |
| Q481-p21 | Crystallization from CHCl$_3$ | Dry Dried at 50° C. u.v. | I |
| Q481-p65-7 | Crystallization from EtOAc | Dry | I |
| Q481-p68-4 | Crystallization from n-pentanol | Dry | I |
| Q481-p72-8 | Crystallization from AcOEt with HCl gas | Dry Dried at 55° C. u.v, | I |
| Q481-p72-9 | Crystallization from AcOEt with HCl gas | Dry Dried at 55° C. u.v, | I |
| Q481-p83-9 | Crystallization from BuOAc | Dry | I |
| Q481-p90-11 | Crystallization from acetone | Dry | I |
| Q481-p90-13 | Crystallization from water | Dry | I |
| Q481-p99-12 | Crystallization from MTBE | Dry | I |
| Q481-p107-5 | Crystallization from dimethylcarbonate | Dry Dried at 50° C. u.v, | I |
| Q481-p113 | Crystallization from n-BuOAc | Dry | I |
| Q481-p114-5 | Crystallization from IPA | Wet | I |
| Q481-p114-6 | Crystallization from IPA | Dry Dried at 50° C. u.v, | I |
| Q481-p134-1 | Crystallization from 2-BuOH | Wet | I |
| Q481-p134-2 | Crystallization from 2-BuOH | Dry | I |

*Samples in Table 2, if not written otherwise, were dried at room temperature and atmospheric pressure.

Example 4

Preparation of Memantine Hydrochloride Form I by Solvent Removal

TABLE 4*

| EXPERIMENT | CONDITIONS | RESIDUE | Crystal form by XRD |
|---|---|---|---|
| Q489-p19-3 | n-BuOH concentration | Wet | I |
| Q489-p19-4 | n-BuOH concentration | Dry | I |
| Q489-p31-2 | n-BuOH concentration | Wet | I |
| Q489-p32-3 | n-BuOH concentration | Dry | I |
| Q481-p128-2 | Solvent evaporation EtOH—CH$_2$Cl$_2$ | Dry | I |
| Q481-p123-2 | Solvent evaporation EtOH | Dry | I |
| Q481-p123-1 | Solvent evaporation EtOH | Wet | I + II |
| Q481-p128-1 | Solvent evaporation EtOH—CH$_2$Cl$_2$ | Wet | I > II |

*Samples in Table 2, if not written otherwise, were dried at room temperature and atmospheric pressure.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A crystalline form of memantine hydrochloride, characterized by at least one of an X-ray powder diffraction pattern having peaks at about 6.7, 13.3, and 20.2±0.2 degrees 2θ; an infrared spectrum having peaks at about 3446, 3396, 2056, 1650, 1621, 1532, 1521, 1384, 1190, 1162, 1061, 1030, 965, 934, and 721 $cm^{-1}$; and a DSC thermogram having endothermic peaks at about 50° C., 90° C., and 341° C.

2. The memantine hydrochloride crystalline form of claim 1, characterized by an X-ray powder diffraction pattern having peaks at about 6.7, 13.3, and 20.2±0.2 degrees 2θ.

3. The memantine hydrochloride crystalline form of claim 2, further characterized by X-ray powder diffraction peaks at about 14.5, 17.2, 18.6, 22.9, 23.9, and 29.0±0.2 degrees 2θ.

4. The memantine hydrochloride crystalline form of claim 3, further characterized by an X-ray powder diffraction pattern substantially as illustrated in FIG. 1.

5. The memantine hydrochloride crystalline form of claim 1, characterized by an infrared spectrum having peaks at about 3446, 3396, 1621, and 1532 $cm^{-1}$.

6. The memantine hydrochloride crystalline form of claim 5, further characterized by infrared peaks at about 2056, 1650, 1521, 1384, 1190, 1162, 1061, 1030, 965, 934, and 721 $cm^{-1}$.

7. The memantine hydrochloride crystalline form of claim 5, characterized by an infrared spectrum substantially as illustrated in FIG. 2.

8. The memantine hydrochloride crystalline form of claim 1, characterized by a DSC thermogram having endothermic peaks at about 50° C., 90° C., and 341° C.

9. The memantine hydrochloride crystalline form of claim 1, characterized by a DSC thermogram substantially as illustrated in FIG. 3.

10. A method for producing the memantine hydrochloride crystalline form of claim 1, comprising: admixing acetone with a solution of memantine hydrochloride and water; removing the water and acetone to obtain said memantine hydrochloride crystalline form; and recovering said memantine hydrochloride crystalline form.

11. The method of claim 10, wherein the ratio of memantine HCl and water is about 0.4 to about 0.6 mol memantine hydrochloride/liter water.

12. The method of claim 10, wherein removing the water and acetone is by maintenance of the mixture for about three days to about three months.

13. The method of claim 10, wherein the admixture is maintained for about one month.

14. The method of claim 10, wherein the solution of memantine hydrochloride and water is heated to a temperature of about 50° C. to 100° C.

15. The method of claim 14, wherein the solution of memantine hydrochloride and water is heated to a temperature of about 80° C. to about 90° C. prior to the admixing of acetone.

16. The method of claim 15, wherein the solution of memantine hydrochloride and water is heated to a temperature of about 85° C. to about 90° C. prior to the admixing of acetone.

17. The method of claim 10, wherein prior to the admixing of acetone, the solution is cooled to a temperature of about 50° C. to about 55° C.

18. A pharmaceutical formulation comprising the memantine hydrochloride crystalline form of claim 1, and a pharmaceutically acceptable excipient.

19. A method of treating a patient suffering from Parkinson's disease or Alzheimer's disease, by administering a therapeutically effective amount of the pharmaceutical formulation of claim 18.

20. A method for producing a memantine hydrochloride crystalline form characterized by X-ray powder diffraction peaks at about 6.3, 12.5, and 18.8±0.2 degrees 2θ, comprising: providing a solution of memantine hydrochloride in $C_{1-4}$ alcohols; exposing the solution to an anti-solvent selected from the group consisting of $C_{1-5}$ ketones and $C_{1-5}$ alkyl esters to obtain a precipitate; and recovering memantine hydrochloride Form I.

21. The method of claim 20, wherein the $C_{1-4}$ alcohol is methanol.

22. The method of claim 20, wherein the $C_{1-5}$ ketone is acetone.

23. The method of claim 20, wherein the $C_{1-5}$ alkyl ester is methyl acetate.

24. The method of claim 20, wherein exposing the solution is by providing an atmosphere saturated with the anti-solvent.

25. A method for producing a memantine hydrochloride crystalline form characterized by X-ray powder diffraction peaks at about 6.3, 12.5, and 18.8±0.2 degrees 2θ, the method comprising: providing a solution of memantine hydrochloride in a solvent selected from the group consisting of water, $C_{1-5}$ alcohols, DMF, and DMSO; and admixing an anti-solvent selected from the group consisting of $C_{6-10}$ aromatic hydrocarbons, open or closed-chained $C_{1-5}$ alkyl ethers, $C_{1-5}$ ketones, $C_{1-5}$ amides, and carbonate esters and amides to cause formation of precipitation; and recovering memantine hydrochloride Form I.

26. The method of claim 25, wherein the solvent is selected from the group consisting of methanol, water, IPA, n-butanol, water, ethanol, DMSO, and DMF.

27. The method of claim 25, wherein the anti-solvent is selected from the group consisting of Toluene, isopropylether, n-BuOAc, AcOEt, acetone, acetonitrile, DMC, THF, MTBE, and MEK.

* * * * *

UNITED STATES PATENT AND TRADEMARK OFFICE
CERTIFICATE OF CORRECTION

PATENT NO. : 7,462,743 B2
APPLICATION NO. : 11/331263
DATED : December 9, 2008
INVENTOR(S) : Merli et al.

Page 1 of 1

It is certified that error appears in the above-identified patent and that said Letters Patent is hereby corrected as shown below:

Column 14
Line 54, change "THE" to --THF--

Signed and Sealed this

Twenty-fifth Day of August, 2009

David J. Kappos
*Director of the United States Patent and Trademark Office*